US012630526B2

(12) United States Patent
Leleti et al.

(10) Patent No.: US 12,630,526 B2
(45) Date of Patent: May 19, 2026

(54) PROCESSES FOR PREPARING AMINOPYRIMIDINE COMPOUNDS

(71) Applicant: ARCUS BIOSCIENCES, INC., Hayward, CA (US)

(72) Inventors: Manmohan Reddy Leleti, Dublin, CA (US); Dillon Harding Miles, Berkeley, CA (US); Brandon Reid Rosen, San Mateo, CA (US); Ehesan Ul Sharif, Menlo Park, CA (US); Jay Patrick Powers, Pacifica, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 835 days.

(21) Appl. No.: 17/609,856

(22) PCT Filed: Jun. 5, 2020

(86) PCT No.: PCT/US2020/036379
§ 371 (c)(1),
(2) Date: Nov. 9, 2021

(87) PCT Pub. No.: WO2020/247789
PCT Pub. Date: Dec. 10, 2020

(65) Prior Publication Data

US 2022/0235031 A1 Jul. 28, 2022

Related U.S. Application Data

(60) Provisional application No. 62/858,050, filed on Jun. 6, 2019.

(51) Int. Cl.
*C07D 401/14* (2006.01)
*C07D 239/42* (2006.01)

(52) U.S. Cl.
CPC ......... *C07D 401/14* (2013.01); *C07D 239/42* (2013.01)

(58) Field of Classification Search
CPC .................................................... C07D 401/14
See application file for complete search history.

(56) References Cited

U.S. PATENT DOCUMENTS

| | | | | |
|---|---|---|---|---|
| 2,778,830 | A | 1/1957 | Pasedach et al. | |
| 7,737,153 | B2 * | 6/2010 | Feurer .................. | C07D 403/12 544/324 |
| 10,399,962 | B2 | 9/2019 | Beatty et al. | |
| 11,072,597 | B2 | 7/2021 | Beatty et al. | |
| 11,478,479 | B2 | 10/2022 | Karakunnel | |
| 11,993,584 | B2 | 5/2024 | Jeffrey et al. | |
| 12,195,447 | B2 | 1/2025 | Beatty et al. | |
| 2022/0235031 | A1 | 7/2022 | Leleti et al. | |
| 2023/0338377 | A1 | 10/2023 | Karakunnel | |

FOREIGN PATENT DOCUMENTS

| | | | | |
|---|---|---|---|---|
| WO | WO-9744326 A1 * | 11/1997 | ........... A61K 31/505 |
| WO | WO-02083652 | 10/2002 | |
| WO | WO-2004104007 | 12/2004 | |
| WO | WO-2010013222 | 2/2010 | |
| WO | WO-2012149157 | 11/2012 | |
| WO | 2018/136700 A1 | 7/2018 | |

OTHER PUBLICATIONS

Khaksar "Fluorinated alcohols: A magic medium for the synthesis of heterocyclic compounds" Journal of Fluorine Chemistry 172 (2015) 51-61.*
Zhang, M. "Carboxylic acid esters: synthesis with retention of the functional group" Science of Synthesis (2006), 20b, 863-946.*
International Search Report mailed Sep. 4, 2020 corresponding to PCT/US2020/036379 filed Jun. 5, 2020; 3 pages.
Written Opinion of the ISA mailed Sep. 4, 2020 corresponding to PCT/US2020/036379 filed Jun. 5, 2020; 5 pages.
Jansa, Petr et al., "5-Substituted 2-amino-4,6-dihydroxypyrimidines and 2-amino-4, 6-dichloropyrimidines: synthesis and inhibitory effects on immune-activated nitric oxide production," *Med Chem Res* (May 9, 2014) 23:4482-4490.
Rosen, Brandon R. et al., "Improved synthesis of sterically encumbered heteroaromatic biaryls from aromatic β-keto esters," *Tetrahedron Letters* (Mar. 19, 2020) 61:151855; 5 pages.
Benderitter et al., 2-Amino-6-iodo-4-tosyloxypyrimidine: a versatile key intermediate for regioselective functionalization of 2-aminopyrimidines in 4- and 6-positions, Tetrahedron 2007, 63, pp. 12465-12470.
B-Rao et al., Identification of novel isocytosine derivatives as xanthine oxidase inhibitors from a set of virtual screening hits, Bioorganic & Medicinal Chemistry 2012, vol. 20, pp. 2930-2939, XP028412821.
Dandia et al. 2,2,2-Trifluoroethanol as Green Solvent in Organic Synthesis: A Review. Mini-Reviews in Organic Chemistry, 2014, 11, 462-476.
Extended European Search Report for European Patent Application No. 20819053.8 dated Apr. 6, 2023. 9 pages.
Santos et al., Anti-parasitic Guanidine and Pyrimidine Alkaloids from the Marine Sponge Monanchora arbuscula, J Nat Prod. 2015;78(5):1101-1112.
Sharif et al., Development of a Scalable and Practical Synthesis of AB928, a Dual A2a/A2b Receptor Antagonist, Organic Process Research & Development 2020, 24, pp. 1254-1261.
Wang et al., Ambient-Light-Promoted Three-Component Annulation: Synthesis of Perfluoroalkylated Pyrimidines, Org. Lett. 2017, 19, pp. 2358-2361, XP093035640.

* cited by examiner

*Primary Examiner* — David K O'Dell
(74) *Attorney, Agent, or Firm* — NORTON ROSE FULBRIGHT US LLP

(57) ABSTRACT

Provided herein are improved processes for preparing aminopyrimidine compounds of Formula (I). The disclosed processes advantageously proceed through a β-diketoester intermediate of Formula (A) and avoid the direct linking of a pyrimidine and phenyl moieties. The disclosed methods significantly increase yield of the desired compounds and simplifies the synthetic route.

19 Claims, No Drawings

PROCESSES FOR PREPARING AMINOPYRIMIDINE COMPOUNDS

CROSS-REFERENCES TO RELATED APPLICATIONS

This application is a national stage application filed under 35 U.S.C. § 371 of International Patent Application No. PCT/US2020/036379, filed Jun. 5, 2020, which claims priority benefit under 35 U.S.C. § 119(e) of U.S. Provisional Application No. 62/858,050, filed Jun. 6, 2019, the disclosures of which are herein incorporated by reference their entireties for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Adenosine is a purine nucleoside compound comprising a complex of adenine and a ribose sugar molecule (ribofuranose). Adenosine occurs naturally in mammals and plays important roles in several biochemical processes, including energy transfer (as adenosine triphosphate and adenosine monophosphate) and signal transduction (as cyclic adenosine monophosphate). Adenosine also serves in processes associated with vasodilation, including cardiac vasodilation, and acts as a neuromodulator (e.g., it is thought to be involved in promoting sleep). In addition to its involvement in these biochemical processes, adenosine is used as a therapeutic antiarrhythmic agent to treat, for example, supraventricular tachycardia. As discussed further herein, tumors evade host responses by inhibiting immune function and promoting tolerance, and adenosine has been shown to play an important role in mediating tumor evasion of the immune system. Adenosine signaling through $A_{2A}$Rs and $A_{2B}$Rs, expressed on a variety of immune cell subsets and endothelial cells, has been established as having an important role in protecting tissues during inflammatory responses. As such, under certain conditions adenosine protects tumors from immune destruction (see, e.g., Fishman, P, et al. (2009) Handb Exp Pharmacol 193:399-441).

The adenosine receptors are a class of purinergic G protein-coupled receptors with adenosine as the endogenous ligand. The four types of adenosine receptors in humans are referred to as $A_1$, $A_{2A}$, $A_{2B}$ and $A_3$. Modulation of $A_1$ has been proposed for the management and treatment of, for example, neurological disorders, asthma, and heart and renal failure; $A_{2A}$ antagonists have been proposed for the management and treatment of, for example, Parkinson's disease; modulation of $A_{2B}$ has been proposed for the management and treatment of, for example, chronic pulmonary diseases, including asthma; and modulation of $A_3$ has been proposed for the management and treatment of, for example, asthma and chronic obstructive pulmonary diseases, glaucoma, cancer, and stroke.

Historically, modulators of adenosine receptors have been nonselective. However, recent more recent work has identified useful adenosine modulators that can specifically target the adenosine $A_{2A}$ receptor ($A_{2A}$R) or the adenosine $A_{2B}$ receptor ($A_{2B}$R). Such work includes the compounds described in WO2018/136700, which include amino pyrimidine moieties.

Despite these advances, the synthetic processes described for preparing the compounds of WO2018/136700 include chemical conversions with lower yields that hinder large scale production and hamper the commercial availability of the compounds.

As such, there is a need in the art for providing improved processes to prepare aminopyrimidine compounds. The present disclosure addresses this need and provides related advantages as well.

BRIEF SUMMARY OF THE INVENTION

In some aspects, provided herein are processes for the preparation of a compound represented by Formula (I):

(I)

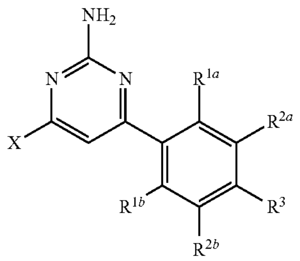

wherein $R^{1a}$, $R^{1b}$, $R^{2a}$, $R^{2b}$, $R^3$ and X are as described herein, said process comprising:

a) contacting a compound of Formula (A)

(A)

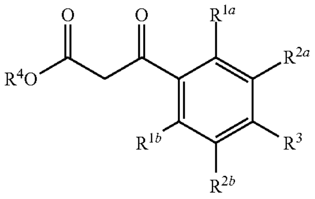

with a guanidine reagent and a solvent system comprising at least one halogenated alcohol to obtain a compound of Formula (B)

(B)

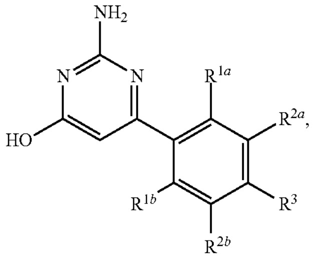

wherein $R^4$ is selected from the group consisting of $C_1$-$C_8$ alkyl and $C_3$-$C_8$ cycloalkyl, each of which is optionally substituted with from 1 to 6 members independently selected from the group consisting of F and Cl; and b) replacing the hydroxy group of Formula (B) to form a compound of Formula In some embodiments, the compound of Formula (I) is a compound of Formula (Ia)

(Ia)

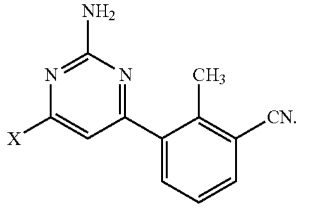

In some aspects provided herein are processes for preparing a compound of Formula (II)

(II)

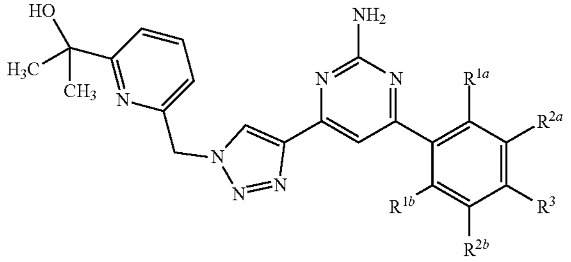

wherein $R^{1a}$, $R^{1b}$, $R^{2a}$, $R^{2b}$, $R^3$ are as described herein, said process comprising:

a') preparing a compound of Formula (I) according to the processes described herein;

b') converting said compound of Formula (I) to a compound of Formula (C);

(C)

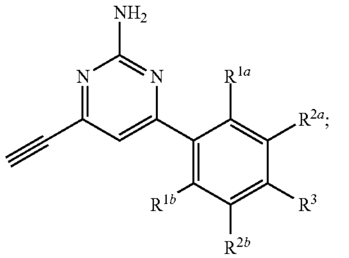

and c') combining said compound of Formula (C) with an azide compound of Formula (D), (D)

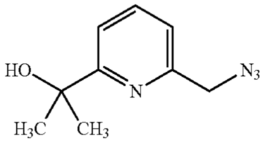

to produce said compound of Formula (II).

In some embodiments, the processes described herein are useful in making a compound of Formula (IIa)

(IIa)

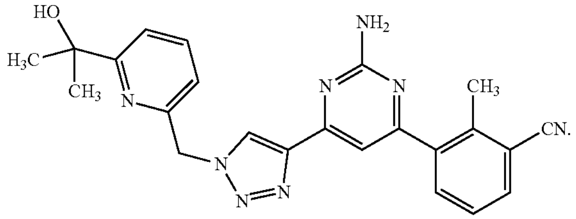

BRIEF DESCRIPTION OF THE DRAWINGS

Not Applicable

DETAILED DESCRIPTION OF THE INVENTION

I. General

The present disclosure provides improved processes for the preparation of aminopyrimidine compounds of Formula (I). In particular, the methods described herein use guanidine and a compound of Formula (A) having a β-diketoester to provide a compound of Formula (B). This conversion advantageously improves the yield for preparing a compound of Formula (B). Subsequent conversion of the alcohol of Formula (B) can be used to prepare compounds of Formula (I).

The methods described herein are particularly useful in the preparation of 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile, but it is understood that the synthetic methods disclosed herein can be used to improve the efficiency and synthetic yields of a number of compounds.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" or "halo" refers to fluorine, chlorine, bromine and iodine.

As used herein, the term "protecting group" refers to a moiety that is formed to render a functional moiety unreactive. The protecting group can be removed so as to restore the functional moiety to its original state. Various protecting groups and protecting reagents, including nitrogen protecting groups, are well known to one of ordinary skill in the art and include compounds that are disclosed in *Protective Groups in Organic Synthesis,* 4th edition, T. W. Greene and P. G. M. Wuts, John Wiley & Sons, New York, 2006, which is incorporated herein by reference in its entirety.

As used herein, the term "basic" is an adjective that refers to a chemical substance that is a base. A basic additive refers to an additive that is a base. A basic reaction condition refers to a reaction condition that includes a pH value above 7.

III. Embodiments of the Disclosure

A. Preparing Compounds of Formula (I)

The inventors of the disclosure have found that combining a Compound of Formula (A) with a guanidine reagent in a solvent system comprising a halogenated alcohol advantageously and efficiently provides the compound of Formula (B) with high yields. Without being bound to any particular theory, it is believed that the electron withdrawing nature of the halo groups in a halogenated alcohol solvent system favor the condensation reaction over alternative reaction products, yielding the compound of Formula (B).

Therefore, in one aspect, provided herein is a process for preparing a compound represented by Formula (I)

(I)

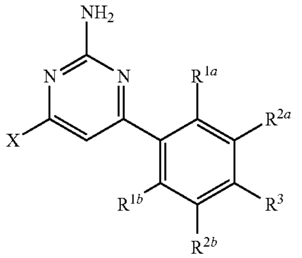

wherein $R^{1a}$ and $R^{1b}$ are independently selected from the group consisting of H, $C_{1-8}$ alkyl, $C_{1-8}$ alkoxy, and halogen;

$R^{2a}$ and $R^{2b}$ are independently selected from the group consisting of H, CN, and halo;

$R^3$ is selected from the group consisting of H, $C_{1-8}$ alkyl, and halogen;

X is a leaving group selected from the group consisting of a halogen and an O-sulfonate ester, said process comprising:

a) contacting a compound of Formula (A)

(A)

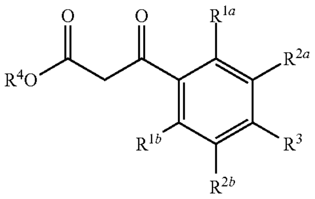

wherein $R^4$ is selected from the group consisting of $C_1$-$C_8$ alkyl and $C_3$-$C_8$ cycloalkyl, each of which is optionally substituted with from 1 to 6 members independently selected from the group consisting of F and Cl;

with a guanidine reagent and a solvent system comprising at least one halogenated alcohol to obtain a compound of Formula (B)

(B)

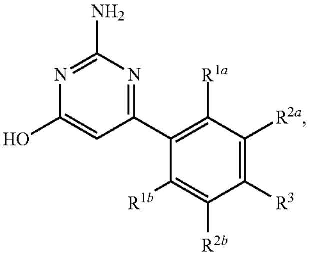

and b) replacing the hydroxy group of Formula (B) to form a compound of Formula (I).

In some embodiments of the process described above, the compound of Formula (I) is a compound of Formula (Ia)

(Ia)

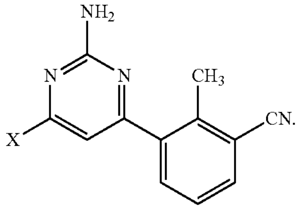

In embodiments where the compound of Formula (Ia) is prepared, step a) includes contacting a compound of Formula (Aa)

(Aa)

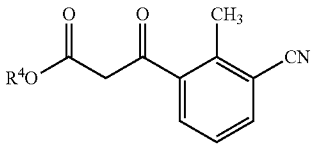

with a guanidine reagent and a solvent system comprising at least one halogenated alcohol to obtain a compound of Formula (Ba)

(Ba)

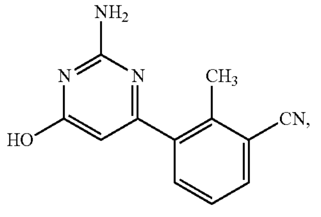

wherein $R^4$ is as defined herein for Formula B.

The phenyl ring having substituents $R^{1a}$, $R^{1b}$, $R^{2a}$, $R^{2b}$, and $R^3$ of the formulas disclosed herein can be any of the substituents described above. In some embodiments, the phenyl ring having the substituents $R^{1a}$, $R^{1b}$, $R^{2a}$, $R^{2b}$, and $R^3$ includes no more than three non-hydrogen moieties. In some embodiments $R^{1a}$ is methyl. In some embodiments $R^{2a}$ is CN. In some embodiments, $R^{1b}$ and $R^{2b}$ are both H. In some embodiments, $R^{1a}$ is methyl, $R^{2a}$ is CN, and $R^{1b}$, $R^{2b}$, and $R^3$ are each H.

In some embodiments, $R^4$ is selected from the group consisting of methyl, ethyl, isopropyl, tent-butyl, and 2,2,2-trifluoroethyl. In some embodiments, $R^4$ is ethyl.

With reference to step a), a guanidine reagent is central to preparing the desired product. There are a number of commercially available sources of guanidine reagents that are useful in the present disclosure. In some embodiments, the guanidine reagent is selected from the group consisting of guanidine, guanidine HCl, guanidine carbonate, guanidine HBr, guanidine nitrate, guanidine HI, guanidine acetate, guanidine sulfate, guanidine bisulfate, guanidine thiocyanate, guanidine sulfamate, guanidine phosphate, and guanidine 4-benzenesulfonate. In some embodiments, the guanidine is guanidine carbonate. In some embodiments the guanidine reagent is guanidine HCl.

As mentioned above, the solvent system comprising at least one halogenated alcohol in step a) directs the favored reaction product towards the condensation product of Formula (B). In some embodiments, the solvent system comprising at least one halogenated alcohol is selected from 2,2,2-trifluoroethanol, 2-fluoroethanol, and 2-chloroethanol. In some embodiments, the solvent system comprising at least one halogenated alcohol is only 2,2,2-trifluoroethanol. In some embodiments, the solvent system comprising at least one halogenated alcohol is a combination of 2,2,2-trifluoroethanol and an alcohol selected from the group consisting of methanol, ethanol, propanol, 2-fluoroethanol, 2-chloroethanol, 2-methoxyethanol, and 2-(methanesulfonyl)ethan-1-ol.

In some embodiments, the conversion of step a) further includes a base. Suitable bases include NaH, NaOH, KOH, LiOH, $Ca(OH)_2$, NaO—$C_{1-8}$alkyl, and KO—$C_{1-8}$alkyl.

The conversion of step a) can be completed at a variety of different temperatures. Typically, step a) is heated to provide high levels of the desired conversion. In some embodiments, step a) is conducted at reflux. In some embodiments, step a) is conducted at a temperature above 70° C. In some embodiments, the conversion of step a) is conducted at a temperature of about 75-105° C. In some embodiments, the conversion of step a) is conducted at a temperature of about 100° C.

The time period for the reaction of step a) will depend on a number of factors including the specific reagents used as well as the temperature. In some embodiments, the reaction of step a) is incubated for about 2, 4, 6, 8, 10, 12, 14, 16, or 18 or more hours. In some embodiments, the reaction of step a) is incubated for about 6 hours. In some embodiments, the reaction of step a) is incubated for about 14 hours.

Yield of the desired product for the conversion of step a) will vary depending on the precise reaction conditions utilized. In some embodiments, the yield of Formula (B) in the conversion of step a) exceeds 60%. In some embodiments, the yield of Formula (B) in the conversion of step a) is at least 65%. In some embodiments, the yield of Formula (B) in the conversion of step a) is at least 70%. In some embodiments, the yield of Formula (B) in the conversion of step a) is at least 75%. In some embodiments, the yield of Formula (B) in the conversion of step a) is at least 80%.

The conversion described in step a) often includes the formation of a small amount of byproduct. The small amount of byproduct formed is the conversion of the compounds of Formula (A) to a compound of Formula (i)

(i)

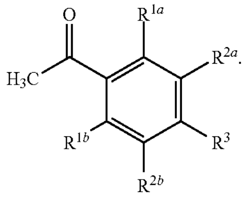

In some embodiments, the byproduct form is a compound of Formula (ia)

(ia)

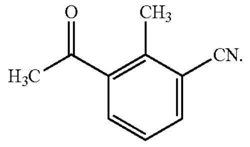

In some embodiments, the methods described herein further include trituration of the byproduct of Formula (i) or (ia) using an organic solvent. Organic solvents useful for the trituration of the undesired byproduct include, but are not limited to, ethanol, methanol, acetonitrile, dichloromethane, ethyl acetate, and methyl tert-butyl ether (MTBE). In some embodiments, the organic solvent used is MTBE or dichloromethane.

A person of skill in the art will recognize that the amount of byproduct formed will depend on the reaction conditions used. Typically, the amount of byproduct formed typically does not exceed 20% of the total amount of Formula (A) converted from starting material. In some embodiments the byproduct formed does not exceed 15% of the total amount of Formula (A) converted from starting material. In some embodiments the byproduct formed does not exceed 10% of the total amount of Formula (A) converted from starting material. In some embodiments the byproduct formed does not exceed 5% of the total amount of Formula (A) converted from starting material.

The modification or replacement of the hydroxyl group of Formula (B) in step b) can be achieved with a number of different reagents. In some embodiments, the hydroxyl is modified through a sulfonation process which provides a compound of Formula (I) wherein X is a sulfonate ester of the hydroxyl group. In some embodiments, step b) includes a halogenation process where the hydroxyl of Formula (B) is replaced with a halogen.

Sulfonation can be achieved using the known sulfonating agents in the art. This includes, but is not limited to methanesulfonyl chloride, triflic anhydride and 4-toluene-sulfonyl chloride.

Halogenation can be achieved using the known halogenation agents in the art. This includes, but is not limited to $POCl_3$, $PSCl_3$, $SOCl_2$, $(COCl)_2$, $PCl_5$, $PBr_3$, N-chlorosuccinimide (NCS) and N-bromosuccinimide (NBS). In some embodiments, the halogenation agent is $POCl_3$.

In some embodiments, the molar ratio of halogenation agent or sulfonating agent to the compound of Formula (B) or Formula (Ba) is controlled. In some embodiments, the molar ratio of halogenation agent or sulfonating agent to the compound of Formula (B) is about 1:1 to about 3:1, or about 1.2:1 to about 1.8:1.

Typically, the solvent system used in step b) is a polar aprotic organic solvent. Suitable polar aprotic organic solvents include, but are not limited to, acetonitrile, DMF, DMSO, NMP and combinations thereof. In some embodiments, the polar aprotic organic solvent is acetonitrile.

In some embodiments, the conversion of step b) further includes a base additive. Suitable bases additives include trimethylamine, diisopropylethylamine, dimethylaniline, benzyltrimethylammonium chloride and benzyltriethylammonium chloride. In some embodiments, the base additive is benzyltriethylammonium chloride The conversion of step b) can be completed at a variety of different temperatures. The preferred temperature will depend on the desired chemical conversion as well as the reagents using used. A person of skill in the art will be able to determine the appropriate temperature based on the chosen reagents. In some embodiments, step b) is conducted at an elevated temperature. In some embodiments, step b) is conducted at a temperature of about 60-90° C. In some embodiments, step b) is conducted at a temperature of about 67-83° C. In some embodiments, step b) is conducted at a temperature of about 70° C. In some embodiments, step b) is conducted at a temperature of about 80° C.

B. Preparing Compounds of Formula (II)

In some aspects, the compound of Formula (I) can be used in the preparation of compounds of Formula (II)

(II)

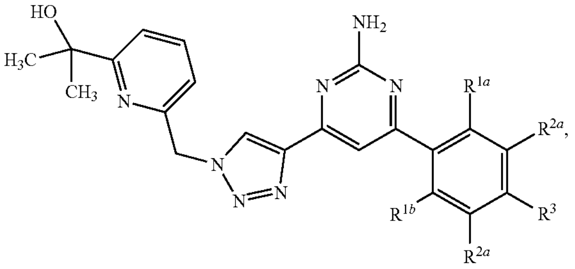

wherein $R^{1a}$ and $R^{1b}$ are independently selected from the group consisting of H, $C_{1-8}$ alkyl, $C_{1-8}$ alkoxy, and halogen;

$R^{2a}$ and $R^{2b}$ are independently selected from the group consisting of H, CN, and halo;

$R^3$ is selected from the group consisting of H, $C_{1-8}$ alkyl, and halogen.

In such embodiments, the process includes:

a') preparing a compound of Formula (I) by contacting a compound of Formula (A)

(A)

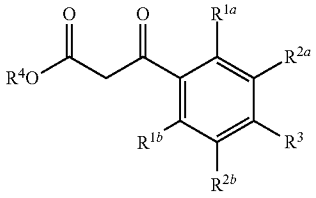

with a guanidine reagent to obtain a compound of Formula (B)

wherein $R^4$ is selected from the group consisting of $C_1$-$C_8$ alkyl and $C_3$-$C_8$ cycloalkyl, each of which is optionally substituted with from 1 to 6 members independently, and replacing the hydroxy group of Formula (B) to form a compound of Formula (I), as described above;

b') converting said compound of Formula (I) to a compound of Formula (C);

(C)

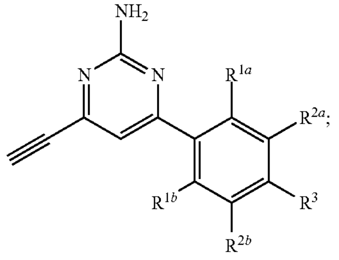

and c') combining said compound of Formula (C) with an azide compound of Formula (D), (D)

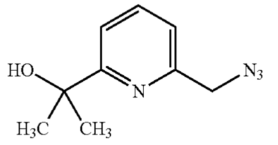

to produce said compound of Formula (II).

In some embodiments in the process described above, the compound of Formula (II) is a compound of Formula (IIa)

(IIa)

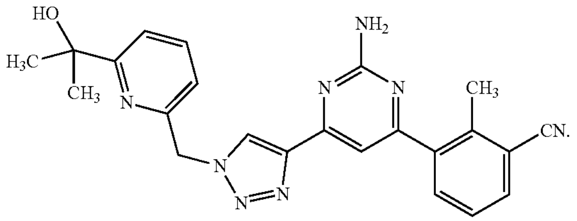

In embodiments where the compound of Formula (IIa) is prepared, a compound of Formula (Ia) is prepared in step a'); step b') converts the compound of Formula (Ia) to a compound of Formula (Ca)

(Ca)

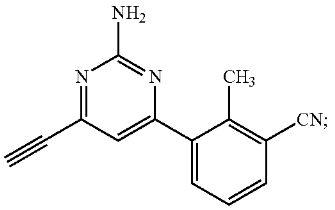

and step c) includes combining the compounds of Formula (Ca) with an azide compound of Formula (D) to produce the compound of Formula (IIa).

After preparing a compound of Formula (I) as described herein, the X position compound of Formula (I) is replaced with an acetylene group, step b'), above. This can be done using any known methods in the art, such as those described in WO2018/136700. In some embodiments, step b') includes sub-steps:

b'-1) contacting the compound of Formula (I) with a silyl protected acetylene with a palladium catalyst and a copper co-catalyst to produce an intermediate of Formula (C'):

(C')

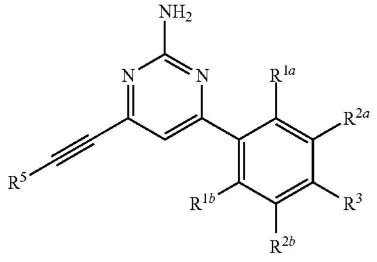

wherein $R^5$ is a silyl protecting group; and b'-2) contacting the compound of Formula (C') with a desilylating reagent to produce said compound of Formula (C).

A variety of palladium and copper catalysts can be utilized in the described conversion. In some embodiments, palladium catalyst is $Pd(PPh_3)_2Cl_2$. In some embodiments, the copper co-catalyst is CuI.

The conversion in step b'-1) can also include base. In some embodiments, the base is an amine base. A number of different amine bases are suitable for this conversion and include, but are not limited to, triethylamine or N,N-diisopropylethylamine.

A number of different organic solvents can be used to carry out the conversion of step b'-1). Suitable organic solvents include tetrahydrofuran, acetonitrile, dichloromethane, ethyl acetate, and methyl tent-butyl ether (MTBE).

The conversion of step b'-1) can be performed at a variety of different temperatures. In some embodiments, the conversion of step b'-1 is performed at a temperature of about 20-90° C. In some embodiments, the conversion of step b'-1 is performed at a temperature of about 30-75° C. In some embodiments, the conversion of step b'-1 is performed at a temperature of about 40-60° C. In some embodiments, the conversion of step b'-1 is performed at a temperature of about 50° C.

Typically, the conversion of step b'-1) is carried out over the course of a few hours, but longer reaction times are also contemplated. In some embodiments, the reaction is incubated for about 1, 2, 3, 4, 5, 6, 7, 8, 9, 10, 11 or 12 or more hours. In some embodiments, the reaction is incubated for about 3 hours. In some embodiments, the reaction is incubated for about 5 hours. In some embodiments, the reaction is incubated for about 7 hours.

The silyl protected acetylene used in step b'-1) can include a number of silyl protecting groups known in the art. Suitable groups include, but are not limited to, triisopropylsilyl, trimethylsilyl, thexyldimethylsilyl, benzyldimethylsilyl, biphenyldiisopropylsilyl, and tris(biphenyl-4-yl)silyl. In some embodiments, the silyl protecting group is triisopropylsilyl.

The conversion of step b'-2) includes removing the silyl protecting group using a desilylating reagent. Many different processes and conditions for removing silyl protecting groups are known in the art and can be used in the process disclosed herein. In some embodiments, the desilylating reagent used is selected from the group consisting of tetra-N-butylammonium flouroide (TBAF), tetrabutylammonium hydroxide, sodium tetrachloroaurate(III), and acetyl chloride. In one embodiment, step b'-2 includes tetrabutylammonium hydroxide (TBAH) (20 mol %) and a $K_2HPO_4$ buffer. In one embodiment, step b'-2 includes tetrabutylammonium hydroxide (20 mol %) and an acetic acid buffer.

Returning to step c') in the process for making a compound of Formula II, this step employs click chemistry to link the azide of Formula (D) and the alkynyl group of Formula (C) to form a tetrazole moiety. Click chemistry is a well described and understood process, and a person of skill in the art can readily identify suitable conditions for performing this reaction. In some embodiments, the reaction of step c') includes a copper catalyst. A variety of copper catalyst can be used in this conversion and include $CuSO_4$, CuI, CuBr, copper (II) triflate and copper (II) acetate. In some embodiments, the copper catalyst is $CuSO_4$.

The azide compound of Formula (D) can be prepared for example, as described in WO2018/136700.

C. Preparing Compounds of Formula (A)

In some aspects, also provided herein are processes for the preparation of compounds having Formula (A)

(A)

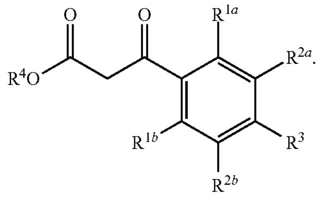

wherein $R^{1a}$ and $R^{1b}$ are independently selected from the group consisting of H, $C_{1-8}$ alkyl, $C_{1-8}$ alkoxy, and halogen;

$R^{2a}$ and $R^{2b}$ are independently selected from the group consisting of H, CN, and halo; and $R^3$ is selected from the group consisting of H, $C_{1-8}$ alkyl, and halogen.

Formula (A) can be prepared from known starting materials. For example, in some embodiments, the compound of Formula (A) is prepared by i) contacting a compound of Formula (a)

(a)

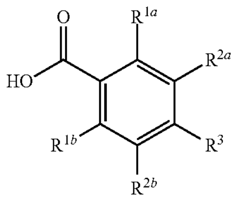

with a halogenation agent to prepare a compound of Formula (b)

(b)

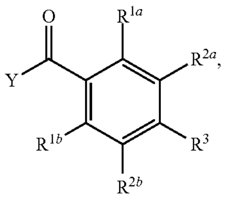

wherein

Y is a halogen;

$R^{1a}$ and $R^{1b}$ are independently selected from the group consisting of H, $C_{1-8}$ alkyl, $C_{1-8}$ alkoxy, and halogen;

$R^{2a}$ and $R^{2b}$ are independently selected from the group consisting of H, CN, and halo; and $R^3$ is selected from the group consisting of H, $C_{1-8}$ alkyl, and halogen;

ii) combining the compound of Formula (b) with a compound of Formula (c)

(c)

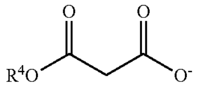

in the presence of a base to form a compound of Formula (A)

(A)

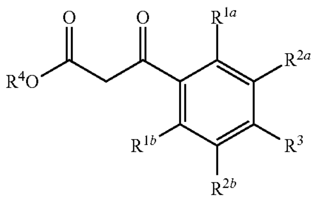

wherein $R^4$ is selected from the group consisting of $C_1$-$C_8$ alkyl and $C_3$-$C_8$ cycloalkyl, each of which is optionally substituted with from 1 to 6 members independently selected from the group consisting of F and Cl.

Halogenation can be achieved using the known halogenation agents in the art. This includes, but is not limited to $POCl_3$, $PSCl_3$, $SOCl_2$, $(COCl)_2$, $PCl_5$, $PBr_3$, N-chlorosuccinimide (NCS) and N-bromosuccinimide (NBS). In some embodiments, the halogenation agent is $(COCl)_2$.

With reference to step ii), the compound of Formula (c) can also be provided in the salt form where a cation is also included. Suitable cations include but are not limited to $K^+$, $Na^+$, and $Li^+$.

A number of bases can be used in step ii). Typically, an amine base is used. A number of different amine bases are suitable for this conversion and include, but are not limited to, pyridine, triethylamine, or N,N-diisopropylethylamine.

In some embodiments, the conversion in step ii) includes a metal catalyst. In some embodiments, the metal catalysts is $MgCl_2$.

In some embodiments, the conversion of step ii) includes cooling the reaction to less than 20° C. prior to combining Formula (b) and Formula (c). In some embodiments, the conversion of step ii) includes cooling the reaction to less than 15° C. prior to combining Formula (b) and Formula (c). In some embodiments, the conversion of step ii) includes cooling the reaction to less than 10° C. prior to combining Formula (b) and Formula (c).

D. Preparing Compounds of Formula (a)

In some aspects, also provided herein are processes for the preparation of compounds having Formula (a')

(a')

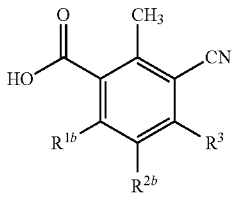

wherein $R^{1b}$ is independently selected from the group consisting of H, $C_{1-8}$ alkyl, $C_{1-8}$ alkoxy, and halogen;

$R^{2b}$ is independently selected from the group consisting of H, CN, and halo; and $R^3$ is selected from the group consisting of H, $C_{1-8}$ alkyl, and halogen.

Compounds having Formula (a') can be prepared for example, in some embodiments by:

i) contacting a compound of Formula (a'y)

(a'y)

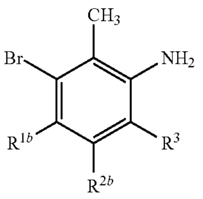

with a cyanation reagent to prepare a compound of Formula (a'x)

(a'x)

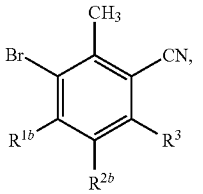

wherein $R^{1b}$ is independently selected from the group consisting of H, $C_{1-8}$ alkyl, $C_{1-8}$ alkoxy, and halogen;

$R^{2b}$ are independently selected from the group consisting of H, CN, and halo; and $R^3$ is selected from the group consisting of H, $C_{1-8}$ alkyl, and halogen; and ii) contacting the compound of Formula (a'y) with a Grignard reagent and $CO_2$ to give the compound of Formula (a'x).

Cyanation can be achieved using known cyanation agents in the art. This includes, but is not limited to, copper-mediated cyanation reagents such as CuCN or $K_3Fe(CN)_6$. In one embodiment, the cyanation is conducted with CuCN in the presence of $NaNO_2$ and HCl.

With reference to step ii), the Grignard reagents are typically of the general formula R—Mg—X, where X is a halogen, and R is an organic carbon group. Examples of Grignard reagents include, but are not limited to methylmagnesium chloride, phenyl magnesium bromide, and isopropylmagnesium chloride. In one embodiment, step ii) is conducted with iPrMgCl, in the presence of LiCl, THF and $CO_2$.

EXAMPLES

Example 1: Trifluoroethanol Assisted Condensation of β-Ketoesters to Provide a Hydroxypyrimidine (and Chloropyrimidine)

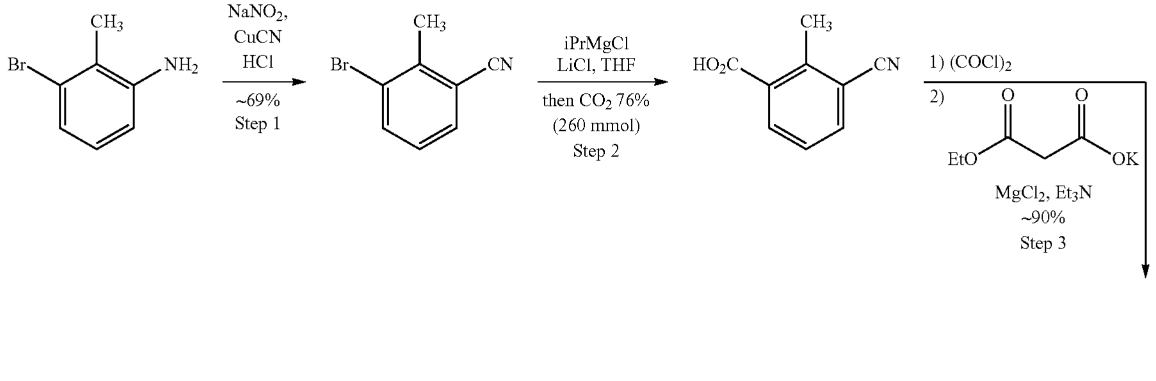

-continued

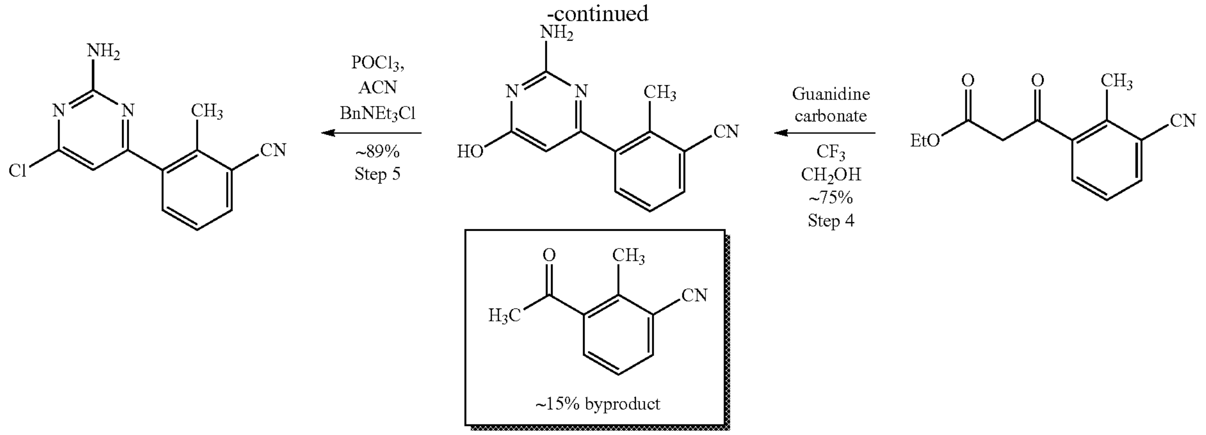

Step 1: To a mixture of 12 M HCl $_{(aq)}$ (26 mL) and water (26 mL) at r.t. was added 3-bromo-2-methylaniline (18.6 g, 100 mmol) dropwise so that a fine white suspension forms. The mixture was cooled to 0° C. and a solution of sodium nitrite (7.31 g, 106 mmol) in water (15.1 mL) was added dropwise. The mixture was stirred at 0° C. for 30 minutes. To the resultant homogeneous mixture at 0° C. was added sodium bicarbonate (17.8 g, 212 mmol) at such a rate to avoid excessive gas evolution. The aqueous phase of the resultant brown suspension was found to have pH ~7. This suspension was maintained at 0° C.

In a separate flask, copper cyanide (9.85 g, 110 mmol), potassium cyanide (13.0 g, 200 mmol), and water (31 mL) were heated to 60° C. to form a homogeneous solution. To this solution at 60° C. with stirring was added the above suspension dropwise to avoid excessive gas evolution. After addition, the mixture was stirred at 100° C. for 30 minutes. The mixture was cooled, MTBE (200 mL) was added, the mixture agitated, and filtered to remove any solids, washing with MTBE. The organic phase was dried over $Na_2SO_4$ and concentrated. The resultant crude product was purified by vacuum distillation to afford the desired product as a light orange solid (13.6 g, 69%).

Step 2: In a two liter two-necked flask, aryl bromide (101.9 g, 520 mmol, 1.0 equiv.) was dissolved in THF (520 mL) under an atmosphere of $N_2$, and the mixture was cooled in an ice-water bath. iPrMgCl·LiCl (400 mL, 1.3 M in THF, 520 mmol, 1.0 equiv.) was added by cannula. Upon completion of the addition, the ice bath was removed. After four hours, the flask was cooled in an ice-water bath and dry ice (~230 g, 5.2 mol, 10 equiv.) was added portionwise to prevent overheating or bubbling over (note: $CO_2$ gas can be bubbled through the solution in place of solid dry ice). When bubbling from the addition was complete, the mixture was diluted with MTBE (500 mL) and 2M HCl (250 mL). The layers were separated, and the aqueous layer was washed with additional MTBE (500 mL). The organic layer was extracted with 10% NaOH (190 mL×2), and the combined aqueous layers were cooled in an ice-water bath and acidified with concentrated HCl until a white precipitate formed. The precipitate was isolated by filtration and washed with water before being dried overnight in a vacuum oven at 80° C. to afford the benzoic acid as a white solid (64.1 g, 76% yield).

Step 3: The benzoic acid (50 g, 311 mmol, 1.0 equiv.) was suspended in $CH_2Cl_2$, and oxalyl chloride (40 mL, 466 mmol, 1.5 equiv.) was added, followed by DMF (~30 drops). Off-gassing was observed immediately, and the reaction flask was open to the atmosphere under positive pressure of $N_2$. Upon complete consumption of the starting acid as determined by LCMS and visual inspection (complete dissolution of starting material), the reaction mixture was concentrated. Excess oxalyl chloride was removed by azeotropic distillation with toluene to afford the corresponding acid chloride as a tannish-brown solid.

In a separate two-necked flask equipped with an overhead stirrer, potassium ethyl malonate (66.1 g, 388 mmol, 1.25 equiv.), triethylamine (108 mL, 777 mmol, 2.5 equiv.) and MeCN (777 mL) were cooled in a salt/ice-brine bath. Solid $MgCl_2$ (74 g, 777 mmol, 2.5 equiv.) was added, and the resulting suspension was vigorously stirred at ~−10° C. After one hour, the solid acid chloride was added at a rate to ensure dissolution into the thick suspension. The suspension rapidly became homogenous, and the stirring rate was reduced to avoid splashing. The ice bath was removed. Upon complete consumption of the starting material as determined by TLC analysis, the reaction mixture was cooled in an ice-water bath, and 2M HCl (971 mL, 1.9 mol, 6.25 equiv.) was added, and the ice bath was removed. After 30 minutes, the layers were separated, and the aqueous layer was extracted with MTBE. The combined organic layers were washed with saturated $NaHCO_3$ and brine, dried over sodium sulfate, filtered, and concentrated to afford the keto-ester as a tannish-brown solid (67 g, 93% yield).

Step 4: A round-bottom flask was charged with 42.0 g (181.8 mmol) of the β-keto-ester, 32.7 g (181.8 mmol) of guanidinium carbonate and 227 mL of trifluoroethanol. The suspension was then heated to reflux under $N_2$ for 16 h.

Work-up: The reaction was cooled to room temperature and solvent was evaporated under reduced pressure to obtain a viscus red oil. The oil was re-dissolved in 250 mL $H_2O$ and the aqueous solution was extracted with dichloromethane (2×250 mL). The aqueous phase is then acidified to pH ~2-3 using 1.0 M $HCl_{(aq.)}$. The precipitated product was collected by filtration, washed thoroughly with $H_2O$ and dried in a vacuum oven at 70° C. Yield 30.81 g (75%), Purity>99%.

Step 5: A round-bottom flask was charged with 50.0 g (221.2 mmol) pyrimidone from step 4 and 100.8 g (442.2 mmol) of benzyltriethylammonium chloride. The mixture was suspended in 442.2 mL of dry acetonitrile and 31.0 mL (331.8 mmol) of $POCl_3$ was added. The suspension thus obtained was then heated to reflux under $N_2$ for 4 h.

Work-up: The reaction was cooled to room temperature and ~200 g crushed ice was added. The mixture was then stirred for 30 min flowed by dropwise addition of ice-cold 15% aqueous $NH_4OH$ to ~pH 10-11. (Note: Slow addition of cold NH4OH is recommended to avoid sudden exotherm due to quenching of excess $POCl_3$). The suspension was then stirred at room temperature for an additional 1.5 h. The precipitated product was collected by filtration, washed thoroughly with $H_2O$ and dried in a vacuum oven at 70° C. Yield 48.2 g (89%), Purity>99%.

HPLC Conditions

HPLC: Agilent 1100

Column: YMC-HPLC Column; 250×4.6; S-5 μm, 20 nm; AQ20S05-2546WT; No. 0425058945

Solvent: $H_2O$/MeCN with 0.1% $HCO_2H$

Flow Rate: 0.8 mL/min

Column Temperature: 30° C.

Method:

| Time | Solvent A ($H_2O$ with 0.1% $HCO_2H$) | Solvent B (ACN with 0.1% $HCO_2H$) |
|---|---|---|
| 0 | 95 | 5 |
| 8 | 95 | 5 |
| 35 | 5 | 95 |
| 45 | 5 | 95 |
| 46 | 95 | 5 |
| 56 | 95 | 5 |

Example 2: Comparative Pyrimidine Coupling

The synthetic route for preparing 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile utilizing boronic ester benzonitrile to linked the phenyl and pyrimidine rings is shown below and is also provided in WO2018/136700.

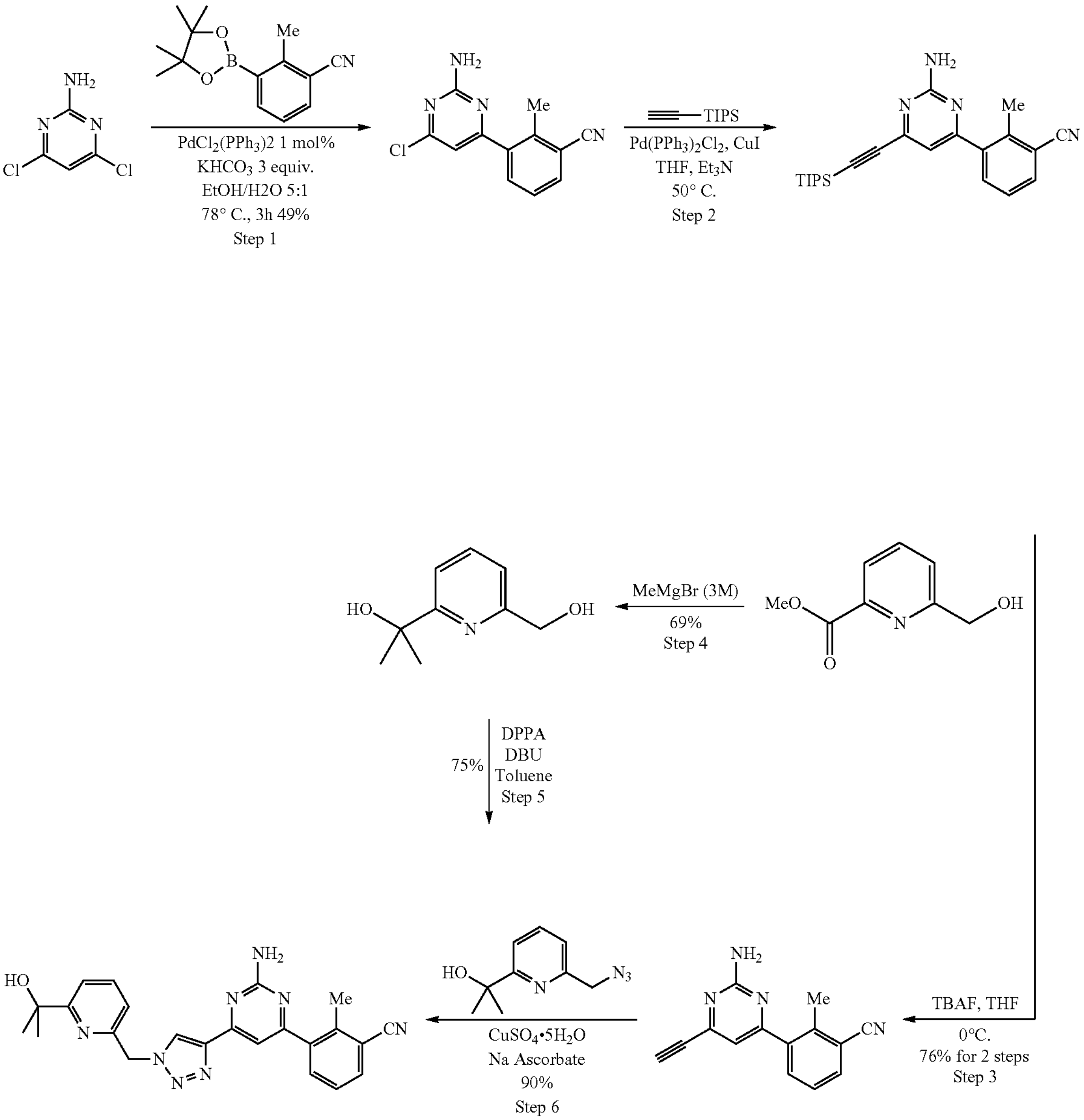

The scheme below displays the synthetic route used to prepare the boronic ester benzonitrile used in the process above and subsequent reaction with pyrimidine to form a compound of Formula (I). Notably, the desired linkage between the pyrimidine and the phenyl provides a yield of less than 50%.

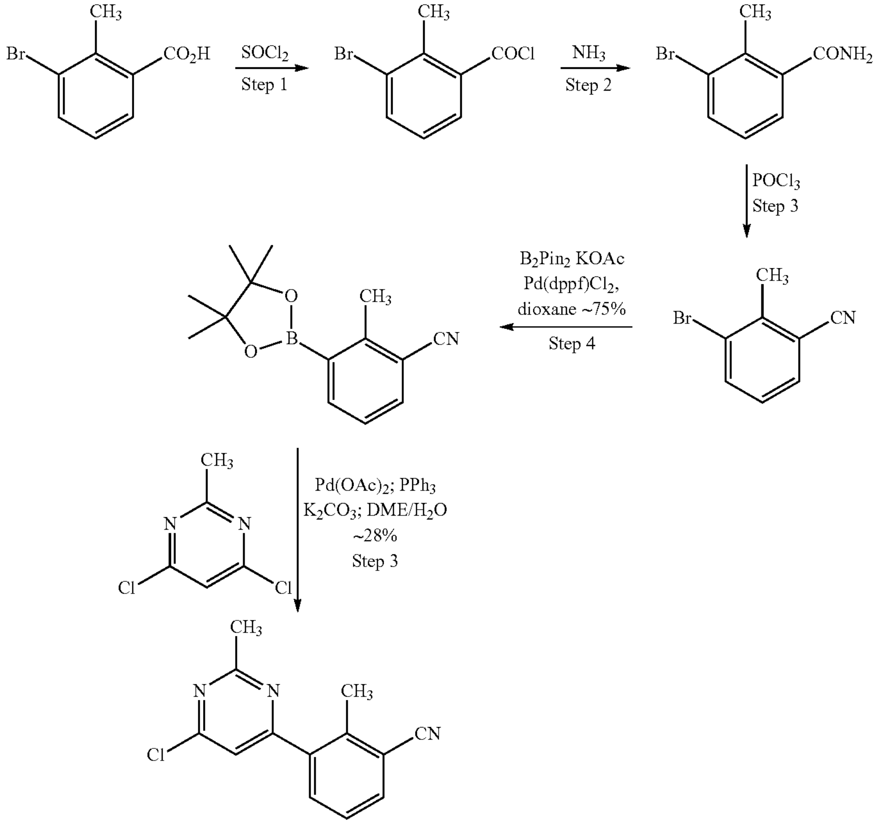

The below scheme displays the synthetic route used to prepare a compound of Formula (I) that utilized a conversion of a β-diketoester to a pyrimidine using guanidine. The route provides a 75% yield.

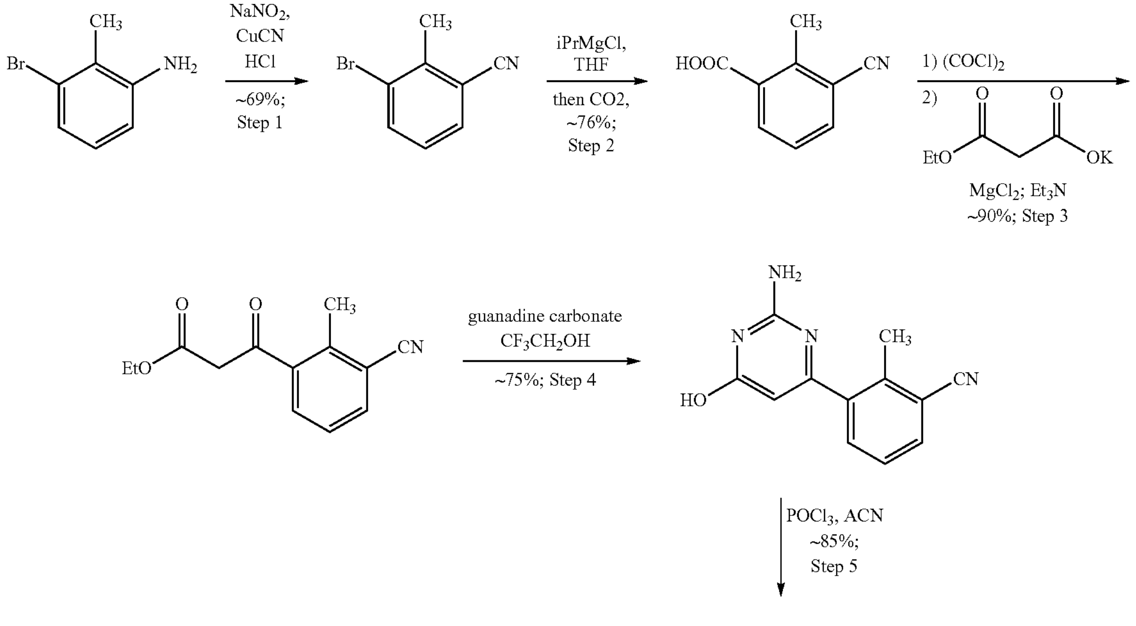

-continued

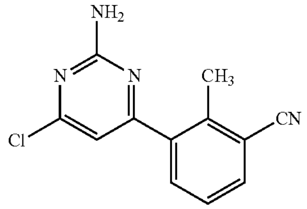

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A process for preparing a compound of Formula (IIa):

(IIa)

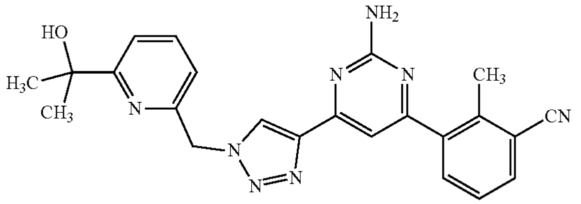

said process comprising:

a') contacting a compound of Formula (A)

(A)

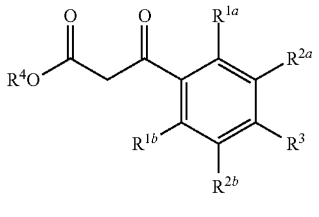

wherein $R^{1a}$ is $CH_3$;

$R^{2a}$ is CN;

$R^{1b}$, $R^{2b}$, and $R^3$ are each H;

$R^4$ is selected from the group consisting of C1-C8 alkyl and C3-C8 cycloalkyl, each of which is optionally substituted with from 1 to 6 members independently selected from the group consisting of F and Cl;

with a guanidine reagent in 2,2,2-trifluoroethanol to obtain a compound of Formula (B)

(B)

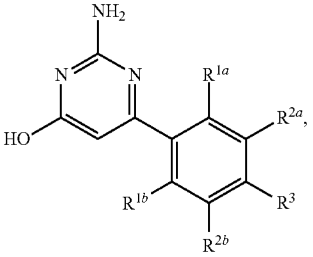

wherein said guanidine reagent is guanidine HCl or guanidine carbonate;

and contacting the compound of Formula (B) with a halogenation agent to form a compound of Formula (Ia)

(Ia)

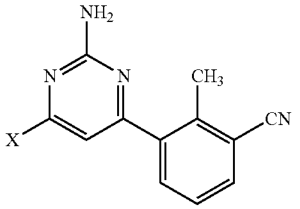

wherein X is Cl or Br and the halogenation agent is $POCl_3$, $PSCl_3$, $SOCl_2$, $(COCl)_2$, $PCl_5$, $PBr_3$, N-chlorosuccinimide (NCS), or N-bromosuccinimide (NBS);

b') converting said compound of Formula (Ia) to a compound of Formula (Ca);

(Ca)

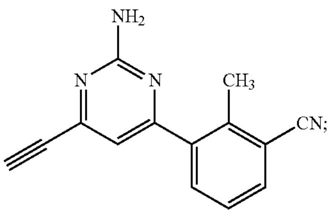

and c') combining said compound of Formula (Ca) with a compound of Formula (D), (D)

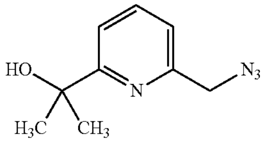

to produce said compound of Formula (IIa).

2. The process according to claim 1, wherein step b') comprises b'-1) contacting the compound of Formula (Ia) with triisopropylsilylacetylene under Sonogashira coupling conditions to produce an intermediate of Formula (Ca'):

(Ca')

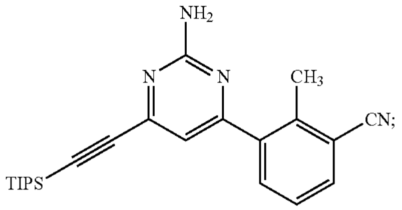

and b'-2) contacting the compound of Formula (Ca') with a desilylating reagent to produce said compound of Formula (Ca).

3. The process according to claim 2, wherein said Sonogashira coupling conditions comprise a palladium catalyst and a copper co-catalyst.

4. The process according to claim 2, wherein said Sonogashira coupling conditions further comprise an amine base.

5. The process according to claim 4, wherein the amine base is triethylamine or N,N-diisopropylethylamine.

6. The process according to claim 2, wherein said desilylating reagent is selected from the group consisting of tetrabutylammonium fluoride (TBAF), tetrabutylammonium hydroxide (TBAH), sodium tetrachloroaurate (III), and acetyl chloride.

7. The process according to claim 1, wherein step c') further comprises a copper catalyst.

8. The process in accordance with claim 1, wherein $R^4$ is selected from the group consisting of methyl, ethyl, isopropyl, tert-butyl, and 2,2,2-rifluoroethyl.

9. The process in accordance with claim 1, wherein contacting the compound of Formula (B) with a halogenation agent is carried out in a polar aprotic organic solvent.

10. The process in accordance with claim 9, wherein said polar aprotic organic solvent is selected from the group consisting of acetonitrile, DMF, DMSO, NMP, and combinations thereof.

11. The process in accordance with claim 9, wherein the halogenation agent is $POCl^3$; X is Cl; said guanidine reagent is guanidine carbonate; and said polar aprotic organic solvent is acetonitrile.

12. The process in accordance with claim 1, wherein contacting the compound of Formula (B) with a halogenation agent is conducted at a temperature of about 67-83° C.

13. The process in accordance with claim 1, wherein said compound of Formula (A), said guanidine reagent, and 2,2,2-trifluoroethanol are heated to reflux temperature.

14. The process in accordance with claim 1, wherein, prior to contacting the compound of Formula (B) with a halogenation agent, said compound of Formula (B) is triturated with an organic solvent to remove a byproduct of Formula (i)

(i)

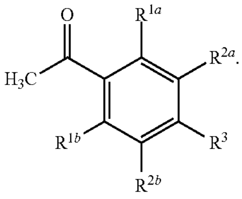

15. The process in accordance with claim 14, wherein said organic solvent is selected from the group consisting of ethanol, methanol, acetonitrile, dichloromethane, ethyl acetate, and methyl tert-butyl ether.

16. The process in accordance with claim 9, wherein contacting the compound of Formula (B) with a halogenation agent is conducted with a base additive.

17. The process in accordance with claim 16, wherein said base additive is selected from the group consisting of trimethylamine, diisopropylethylamine, dimethylaniline, benzyltrimethylammonium chloride, and benzyltriethylammonium chloride.

18. The process in accordance with claim 1, wherein the compound of Formula (A) is prepared by:

i) contacting a compound of Formula (a)

(a)

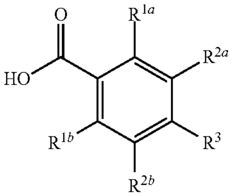

with a halogenation agent to prepare a compound of Formula (b)

(b)

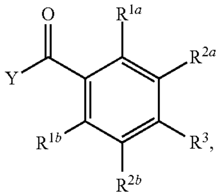

wherein

Y is a halogen; and ii) combining the compound of Formula (b) with a compound of Formula (c)

(c)

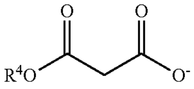

in the presence of a base to form a compound of Formula (A).
19. The process in accordance with claim 18, wherein the compound of Formula (a) is prepared by:
i) contacting a compound of Formula (a'y)
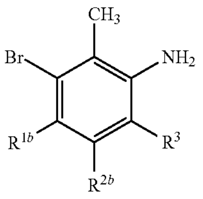
(a'y)
with a cyanation reagent to prepare a compound of Formula (a'x)
(a'x)
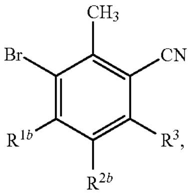
or
ii) contacting the compound of Formula (a'y) with a Grignard reagent and $CO_2$ to give the compound of Formula (a'x).
* * * * *